Figure 1:
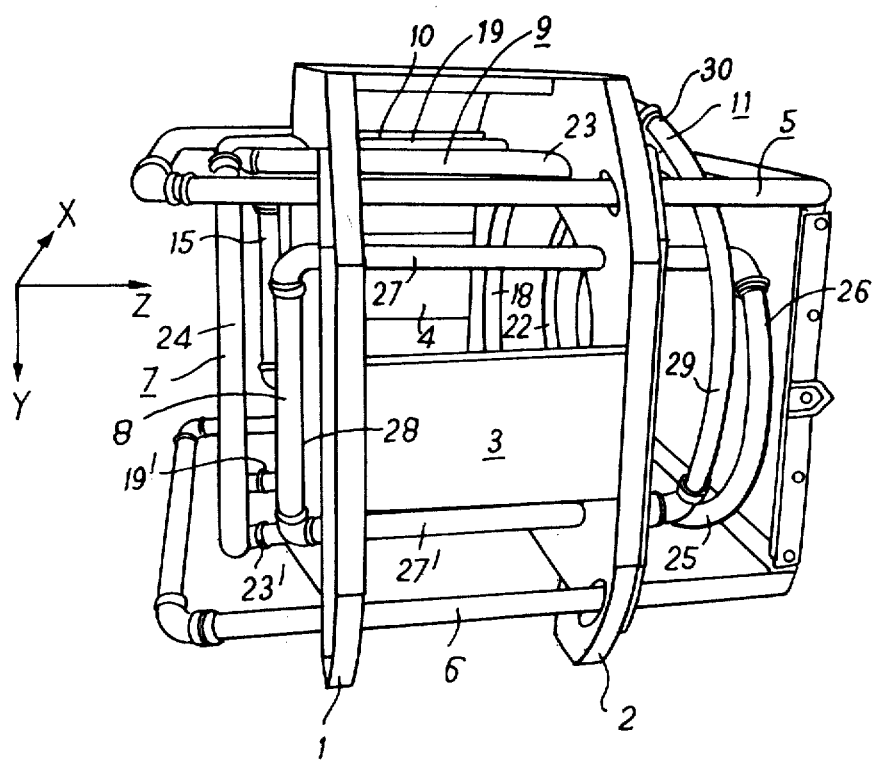

United States Patent [19]

Young et al.

[11] 4,362,993
[45] Dec. 7, 1982

[54] IMAGING SYSTEMS

[75] Inventors: Ian R. Young, Sunbury-on-Thames; Michael Burl, Iver; Graham J. Clarke, Hayes, all of England

[73] Assignee: Picker International Limited, Wembley, England

[21] Appl. No.: 175,674

[22] Filed: Aug. 5, 1980

[30] Foreign Application Priority Data

Aug. 10, 1979 [GB] United Kingdom ............... 7927970

[51] Int. Cl.³ .......................................... G01N 27/00
[52] U.S. Cl. .................................. 324/309; 324/319; 324/320
[58] Field of Search ..................... 324/300, 318–320

[56] References Cited

U.S. PATENT DOCUMENTS 2,507,301  5/1950  Fulbright ......................... 324/319
3,582,779  1/1966  Bloom ............................. 324/320

FOREIGN PATENT DOCUMENTS 1135332  12/1968  United Kingdom ............... 324/320

Primary Examiner—Michael J. Tokar
Attorney, Agent, or Firm—Fleit & Jacobson

[57] ABSTRACT

The invention provides RF field coils and detector coils for an NMR machine. The two coils are specially designed for their respective purpose, the transmit coil (5, 6) being rectangular and the received coil (7-11) substantially elliptical with defined axis ratios and spacing in the z-direction being by projection of equi-spaced conductors on to the ellipse.

21 Claims, 5 Drawing Figures

IMAGING SYSTEMS

The present invention relates to systems for providing images of distributions of a quantity, in a chosen region of a body, by gyromagnetic resonance, for example nuclear magnetic resonance (NMR) techniques. Such techniques may be used for examining bodies of different kinds. However a particularly beneficial application is the examination of patients for medical purposes.

Nuclear magnetic resonance is known for the analysis of materials, particularly by spectroscopy. Recently it has been suggested that the techniques be applied to medical examination to provide images of distributions of water content or relaxation time constants in sectional slices or volumes of patients. Such distributions are similar to, although of different significance from, the distributions of x-ray attenuation provided by computerised tomography (CT) systems.

Practical NMR systems operate by applying suitable combinations of magnetic fields to the body being examined, via coil systems, and detecting induced currents in one or more detector coil systems.

For the examination of a sample of biological tissue, NMR primarily relates to protons, (hydrogen nuclei) in the tissue. In principle however, other nuclei could be analysed, for example, those of deuterium, tritium, fluorine or phosphorus.

Protons each have a nuclear magnetic moment and angular momentum (spin) about the magnetic axis. If a steady magnetic field (typically called $H_{zo}$) is applied to the sample the protons align themselves with the magnetic field, many being parallel thereto and many being anti-parallel so that the resultant spin vector is parallel to the field axis. Application of an additional field $H_1$ which is an R.F. field of frequency related to $H_{zo}$, in a plane normal to $H_{zo}$, causes resonance at that frequency so that energy is absorbed in the sample. The resultant spin vectors of protons in the sample then rotate from the magnetic field axis (z-axis) towards a plane orthogonal thereto (x,y). The R.F. field is generally applied as a pulse and, if $\int H_1 \, dt$ for that pulse is sufficient to rotate the resultant spin vectors through 90° into the x,y plane the pulse is termed a 90° pulse.

On removal of the $H_1$ field the equilibrium alignments re-establish themselves with a time constant $T_1$, the spin-lattice relaxation time. In addition a proportion of the absorbed energy is re-emitted as a signal which can be detected by suitable coils, at a resonant frequency. This resonance signal decays with a time constant $T_2$ (sometimes called $T_2^*$ to distinguish from the spin-spin relaxation time) and the emitted energy is a measure of the proton content of the sample, As so far described, the resonance signal detected relates to the entire sample. If individual resonance signals can be determined for elemental samples in a slice or volume of a patient then a distribution of proton densities, in effect of water content, can be determined for that slice or volume. Additionally or alternatively it is possible to determine the spatial distribution of $T_1$ or $T_2$.

In general the principles of analysing proton density by NMR in a slice of a body have been extensively discussed. The known techniques have been reviewed by P. Mansfield in Contemp. Phys. 17 (b) 1976, 553–576. Consequently the techniques will only be discussed in detail herein to the extent necessary to understand the improved arrangement of this invention.

If it is desired to examine a slice of the patient's body, the first step is to ensure that resonance occurs at the chosen frequency only in the selected slice. Since the resonance frequency (the Larmor frequency) is related to the value of $H_{zo}$, the slice selection is achieved by imposing a gradient on $H_{zo}$ so that the steady field is of different magnitude in different slices of the patient. The steady and uniform $H_{zo}$ field is applied as before, usually longitudinal to the patient (i.e. with the z axis running along the length of the patient). An additional magnetic field $G_z$ is also applied, being a gradient $G_z = \partial H_z / \partial z$. If then the pulsed $H_1$ field is applied at the appropriate frequency, resonance only occurs in that slice in which the resonance frequency as set by $H_{zo}$ and the local value of $G_z$ is equal to the frequency of $H_1$. If the $H_1$ pulse is a 90° pulse, it brings the spin vectors into the x,y plane only for the resonant slice. Since the value of the field is only significant during the $H_1$ pulse, it is only necessary that $G_z$ be applied when $H_1$ is applied, and in practice therefore $G_z$ is also pulsed. The $H_1$ and $G_z$ fields are therefore then removed. It is still, however, possible to change the resonant frequencies of the spin vectors which are now in the x, y plane. This is achieved by applying a further field gradient $G_R$, (actually $\partial H_z / \partial R$) which is parallel to $H_{zo}$. The intensity of $G_R$, however, varies from a maximum at one extreme of the slice, through zero in the centre to a maximum in the reverse direction on the opposite surface. Correspondingly the resonant frequencies will vary smoothly over the plane of the slice from one side to the other.

As mentioned before, the signal which now occurs is at the resonant frequency. Consequently the signals received from the slice will also have frequencies which vary across the slice in the same manner. The amplitude at each frequency then represents inter alia, the proton density in a respective strip of a set of strips parallel to the zero plane of $G_R$. The amplitude for each strip can be obtained by varying the detection frequency through the range which occurs across the slice. Preferably however the total signal at all frequencies is measured. This is then Fourier analysed by well known techniques to give a frequency spectrum. The frequency appropriate to each strip will be known from the field values used and the amplitude for each frequency is given by the spectrum.

It will be apparent that by changing the orientation, relative to the x, y plane, of the zero plane of $G_R$, further sets of signals can be obtained representing proton densities along lines of further sets of parallel strips at corresponding further directions in the examined slice. The procedure is therefore repeated until sufficient data have been derived to process, for example by methods such as those described in British Patent Specifications Nos. 1283915 and 1471531 in connection with the processing of sets of x-ray beams in computerised tomography. In practice the $G_R$ is provided by combination of two fields $G_x$ and $G_y$, which are both parallel to $H_z$ but have gradients in orthogonal directions. The direction of the gradient of the resultant $G_R$ is therefore set by the relative magnitudes of $G_x$ and $G_y$.

The full examination for each direction of the $G_R$ gradient, is achieved by applying the fields (other than $H_{zo}$, which is a steady field) as pulses in a given sequence to various field coils. One especially beneficial pulse sequence is described and claimed in British patent application No. 22291/78 although this invention is not limited in its application to systems utilising that pulse sequence.

The present invention is especially concerned with the construction of the field coils for applying the R.F. field $H_1$ to the patient's body, and also with the construction of suitable coils for detecting the energy re-emitted from the body.

According to the invention there is provided for a nuclear magnetic resonance apparatus for imaging at least one planar section of the body of a patient, a combination of a transmitting coil arrangement, for transmitting radio frequency energy to excite nuclei in said body and a receiving coil arrangement, for receiving radio frequency signals emitted by nuclei excited to resonance wherein the transmitting coil arrangement is of rectangular shape and the receiving coil arrangement is a saddle shaped coil having a plurality of conductors disposed perpendicularly to the plane of said section and distributed substantially uniformly about an ellipse parallel to said section and wherein the transmitting coil arrangement extends beyond the receiving coil arrangement in both directions perpendicular to the plane of said section.

Figure 2:
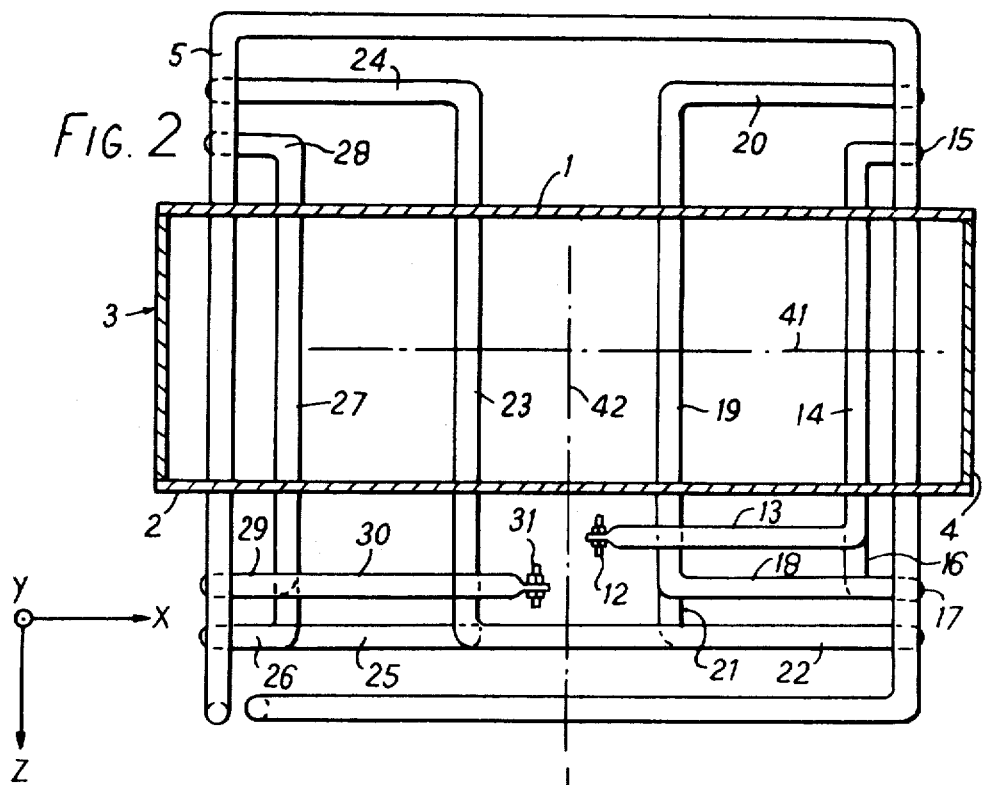
Figure 3:
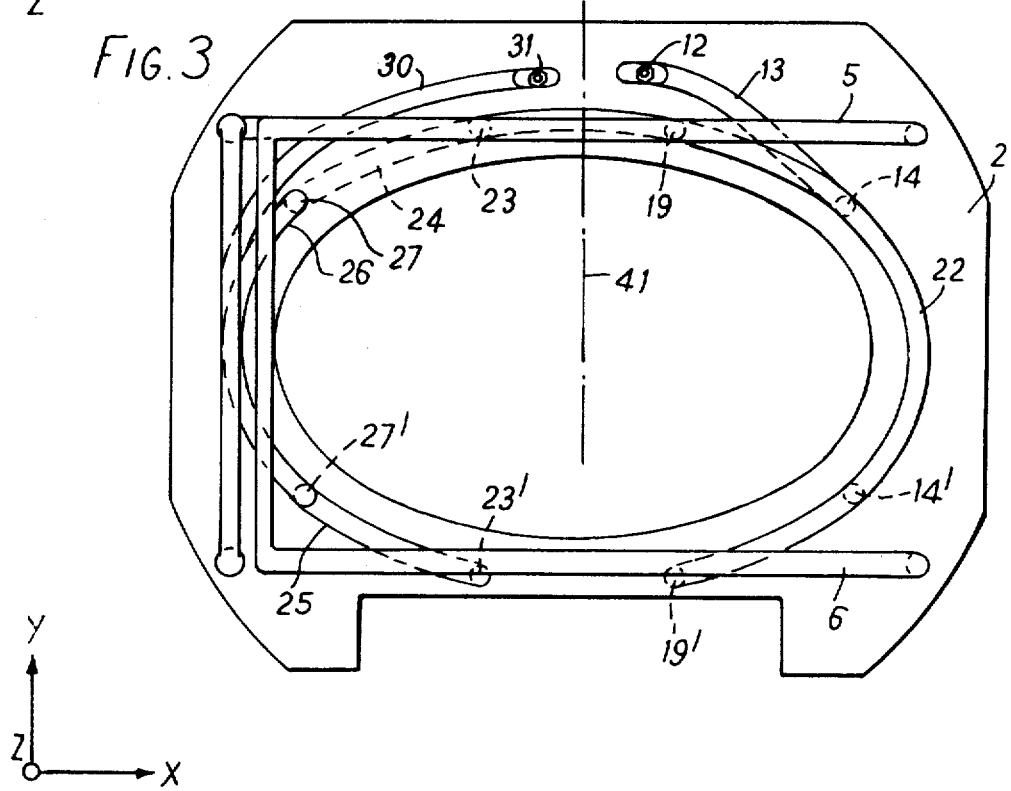
Figure 4:
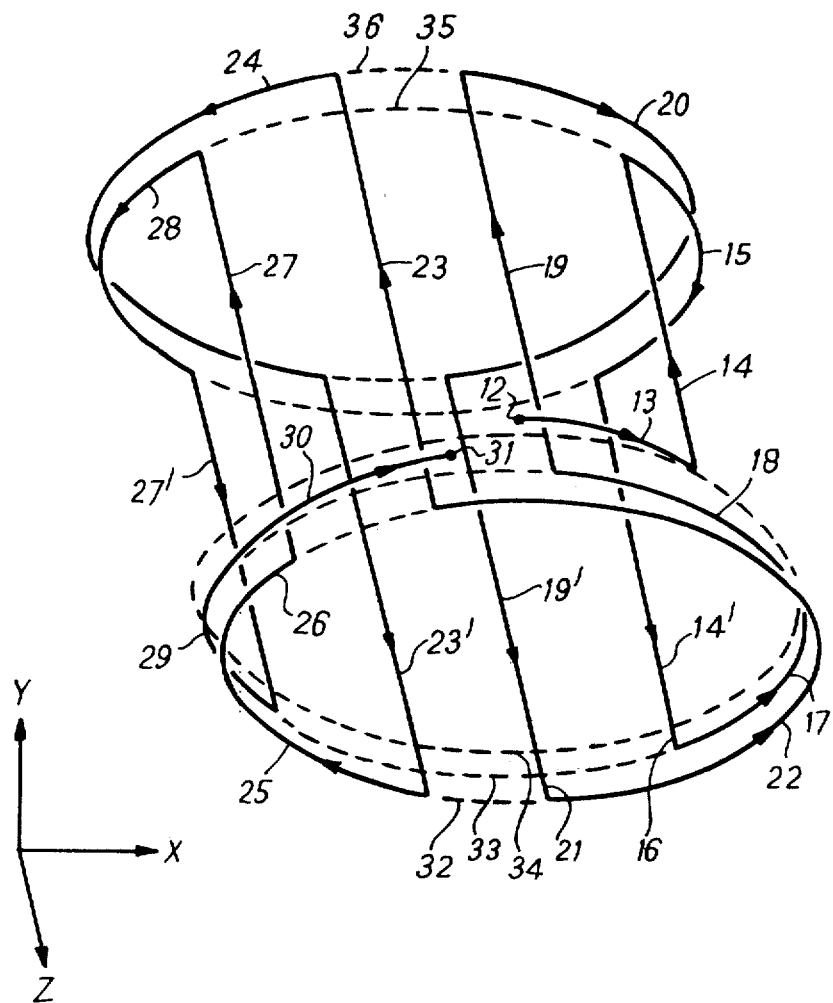
Figure 5:
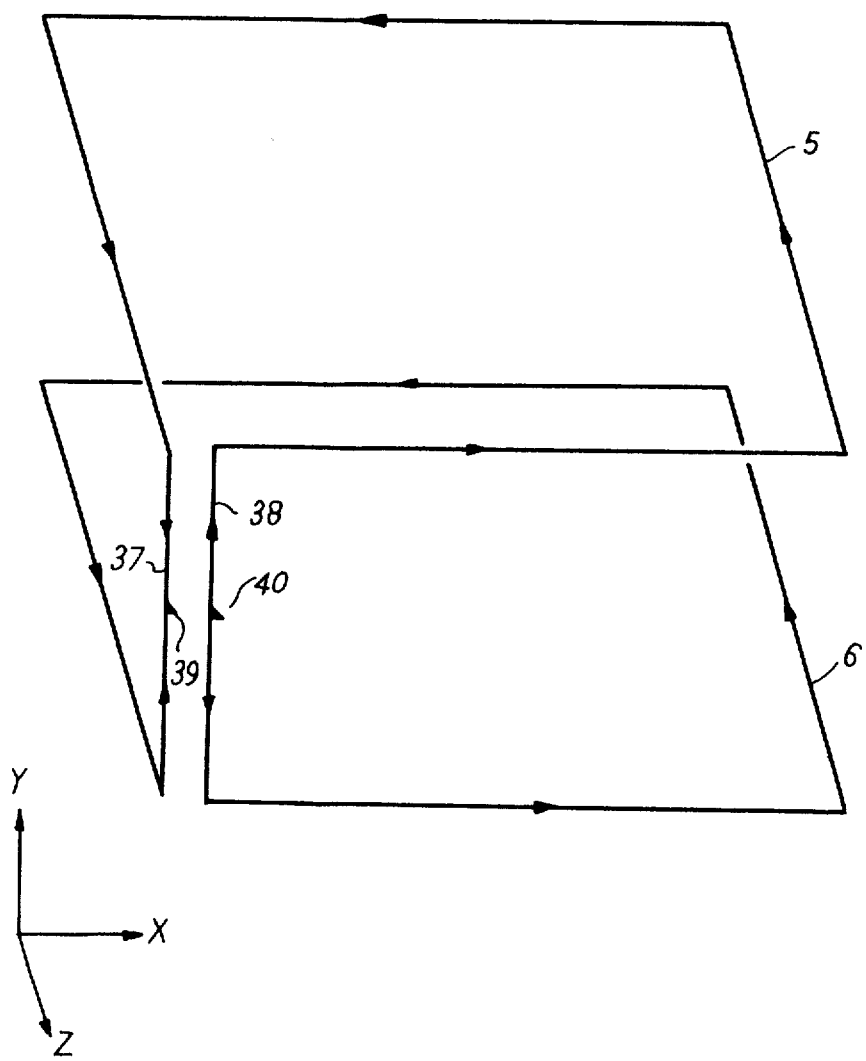

In order that the invention may be clearly understood and readily carried into effect, one embodiment thereof will now be described, by way of example only, with reference to the accompanying drawings, of which:

FIG. 1 shows a perspective view of a set of RF transmit and receive coils in accordance with one example of the invention, FIG. 2 shows the coils in diagrammatic plan view, FIG. 3 shows the coils in diagrammatic end elevation, FIG. 4 shows the receive coil in highly schematic line perspective view, and FIG. 5 shows in similar view to FIG. 4, the transmit coil.

Referring now to the drawings, each of which carries a reference set of co-ordinate axes to assist in the correlation of the various views, with the z-direction being assumed to run longitudinally of the patient, FIG. 1 shows a set of RF transmit and receive coils in accordance with one example of the invention. This figure was derived from a photograph of coils actually constructed, but extraneous detail has not been included to avoid undue complication of the drawing.

The coils are supported on a suitable former constructed of non-magnetic material. In this example the former is constructed of wood and consists of two members 1 and 2, disposed transversely to the Z-direction, the members 1 and 2 being apertured to accommodate a patient's body and otherwise shaped for constructional and assembly reasons. The members 1 and 2 linked by side-supports 3 and 4.

The transmit coil includes coil portions 5 and 6 arranged in rectangular format in the x - z plane above and below the position to be adopted by the patient's body. The receive coil is elliptical in elevation, with its major axis in the x-direction and its minor axis in the y-direction. It may be generally described as 'saddle-shaped' although its longitudinal conductors are distributed substantially uniformly around the ellipse rather than grouped in the manner of a conventional saddle-shaped coil. Some coil portions of the receive coil are shown generally at 7–11 but most portions carry other reference numbers which are consistent with the numbering used in other figures.

FIGS. 2 and 3 show, respectively, plan and end elevational views of the two coils together. Only the upper coil portion 5 of the transmit coil can be seen in FIG. 2, and only the portions of the receive coil which extend longitudinally generally above the patient can be seen. It may be helpful to identify the various limbs of the receive coil and it is proposed to start at terminal 12. Terminal 12 is coupled to a transverse coil portion 13, which bends to run along the patient's body (portion 14) and then bends outwardly (portion 15) around and beneath the patient's body and returns directly beneath the portion 14, extending just beyond portion 14, as shown at 16, and then out around the patient's body (portion 17) and transversely as portion 18. This latter portion bends to run along the patient's body (19), then out and around and below the patient's body (20) returning along the body directly under the portion 19, extending slightly beyond portion 19, as at 21, and then out, up and around the patient's body as shown at 22, crossing over the centre line of the system and bending around to run along the patient's body as at 23, symmetrically with the portion 19. Portion 23 bends around to the left, goes across (24) around and below the patient's body, returning along the body directly beneath portion 23, turning out across the patient (25), then around and above the patient (26) and runs along the patient's body as at 27, symmetrically with the portion 14. Portion 27 bends out left (28), goes around and below the patient, returns along the patient directly below the portion 27, then bends out left (29) up and across the patient, as shown at 30, and is connected to the other terminal 31.

The same numbering system has been used in FIG. 3, where appropriate, and the convention has been adopted of showing coil portions that were obscured from view in FIG. 2, because they were directly beneath other coil portions, with the number of the obscuring portion primed. Thus, in FIG. 3, the portion shown at 19' is that which was obscured by the portion 19 in FIG. 2 and so on. The same numbering system is also used in the perspective line drawing of FIG. 4, which also illustrates in dashed lines the completed ellipses to which the various transverse coil portions conform. In this example, the ellipses are all parallel and displaced from one another in the Z-direction. The three ellipses at one end are denoted by the reference numbers 32–34 and the two at the other end are denoted by the reference numbers 35 and 36.

The rectangular transmit coil is much simpler to visualise and it will therefore not be described in great detail. Suffice to say, with reference to FIGS. 2, 3 and 5, that the upper and lower coil portions 5 and 6 are linked at one corner by arms 37 and 38 extending in the y-direction and that connecting terminals such as 39 and 40 are provided in the linking arms.

It will be observed from FIG. 2 particularly that the transmit coil extends, in the Z-direction, beyond the receive coil. The total extent of the transmit coil in the Z-direction, measured from the mid-point of the transverse portions of the coil disposed at opposite ends of the system, is 560 mm whereas the corresponding extent of the receive coils (i.e. the distance between the front and rear ellipses 32 and 36) is 450 mm. The distance between the ellipses 33 and 35 is 360 mm and the distance of the ellipse 34 from the transverse centre line 41 of the coil system is 135 mm. Typically, the lateral extents of the transmit and receive coils in the x-direction are substantially equal (560 mm in this example) and the ratios of major axis to minor axis of the various ellipses are all the same and in the range 1.3–1.8 (typically 1.6) for body-scanning and in the range 1.0 to 1.4 (typically 1.2) for head scanning. These values are chosen to effect tight coupling by ensuring that the coils are made as small as possible. Notwithstanding the values given for ratios of major to minor axes in preferred embodiment, the invention is not to be limited to the precise mathematical shape known as an ellipse. Other oval shapes are envisaged to be included and in one extreme for head scanning an ellipse of ratio 1.0 (a circle) is included.

The spacing of the Z-direction conductors, such as 14, 19, 23, 27 and 14', 19', 23' and 27', of the receive coil described hereinbefore as substantially uniform is determined by projecting a plane of equi-spaced conductors on to the ellipse. This can be done for any number of conductors, but four pairs is at present considered to be the optimum for the frequency range 2–13 MHz.

The conductors are made as large as possible, to minimise losses, and in one practical example were constructed of 22 mm diameter copper pipe.

With regard to the transmit coil, the ratio of coil side length to the spacing between the two coils is in the range 1.40 to 1.70, typically 1.55. This coil produces a uniform field in the y-direction while the receiver coil is uniformly sensitive to the x-direction field. The orthogonality between the two coils is advantageous for the NMR system as a whole and it can be seen from the drawings that the overall system is physically compact. Uniformity of sensitivity of the receiver coil can be determined in practice by using the coil for test purposes as a transmitter coil and measuring the uniformity in the x-direction of the field created. If this is sufficiently uniform then the receiving sensitivity will also be adequately uniform.

Again with regard to the transmit coil, the two coil portions 5 and 6 can, if desired, be connected in series, instead of in parallel as shown in FIG. 5. The transmit coil is also preferably constructed of copper pipe of diameter 22 mm or greater. The transmit coil shown has about the same uniformity, in the plane (x-y) of the examined slice, as a saddle-shaped coil of the same dimensions, but the z-direction uniformity is substantially greater than for such a saddle-shaped coil.

Returning again to the receive coil, it can be seen that, as shown in FIG. 2, the four pairs of conductors which extend in the z-direction are disposed with their projections on the major ellipse axis at ±0.25a and ±0.75a from the longitudinal centre line 42 of the system, where 2a is the major ellipse dimension. In some circumstances, it can be preferable to bring the conductors closer together, for example to positions at ±0.2a and ±0.6a. In general, if the projections are at ±na and ±3na, n preferably lies between 0.167 and 0.250.

What we claim is:

1. For a nuclear magnetic resonance apparatus for imaging at least one planar section of the body of a patient, a combination of a transmitting coil arrangement, for transmitting radio frequency energy to excite nuclei in said body and a receiving coil arrangement, for receiving radio frequency signals emitted by nuclei excited to resonance, wherein the transmitting coil arrangement is of rectangular shape and the receiving coil arrangement is a saddle shaped coil having a plurality of conductors disposed perpendicularly to the plane of said section and distributed substantially uniformly about an ellipse parallel to said section and wherein the transmitting coil arrangement extends beyond the receiving coil arrangement in both directions perpendicular to the plane of said section.

2. A combination according to claim 1 wherein the transmitting coil arrangement is adapted to produce a uniform magnetic field in one direction in the plane of said section and the receiving coil arrangement is adapted to be uniformly sensitive in the orthogonal direction in the plane of said section.

3. A combination according to claim 1 wherein the receiving coil arrangement is arranged to have uniform sensitivity in one direction in the plane of said section by having conductors spaced around said ellipse so as to be of equal spacing as projected on said direction.

4. A combination according to claim 3 wherein said direction of uniform sensitivity is the major axis of said ellipse.

5. A combination according to claim 4 wherein the receiving coil arrangement includes four pairs of conductors disposed perpendicularly to the plane of said section with their projections on the major axis of said ellipse being at ±na and ±3na where 2a is the major axis ellipse dimension.

6. A combination according to claim 5 wherein n is between 0.167 and 0.250.

7. A combination according to claim 1 wherein the transmitting coil arrangement comprises two spaced rectangular coil parts.

8. A combination according to claim 7 wherein the ratio of the length of said coils, perpendicular to the plane of said section, to their spacing is in the range 1.40 to 1.70.

9. A combination according to claim 8 wherein said ratio is 1.55.

10. A combination according to any one of claims 7, 8 or 9 wherein the coil parts are electrically connected in parallel.

11. A combination according to claim 1 wherein the said coil arrangements comprise metal pipe conductors.

12. A combination according to claim 11 wherein the metal is copper.

13. A combination according to any one of claims 11 or 12 wherein the pipe is 22 mm diameter.

14. A combination according to claim 1 for scanning the torso of a patient wherein the ratio of major to minor axes of the ellipse is between 1.3 and 1.8.

15. A combination according to claim 14 in which said ratio is 1.6.

16. A combination according to claim 1 for scanning the head of a patient wherein the ratio of major to minor axes of the ellipse is between 1.0 and 1.4.

17. A combination according to claim 16 wherein said ratio is 1.2.

18. In combination, a transmitting coil arrangement for transmitting radio frequency energy and a receiving coil arrangement for receiving radio frequency energy, wherein the transmitting coil arrangement is of rectangular shape including conductors substantially perpendicular to a plane and the receiving coil arrangement is a saddle shaped coil having a plurality of conductors perpendicular to said plane and distributed substantially uniformly about an ellipse in said plane and wherein the transmitting coil arrangement extends beyond the receiving coil arrangement in both directions perpendicular to said plane.

19. A combination according to claim 18 in which the receiving coil arrangement includes a plurality of pairs of said conductors disposed with their projections at equal spacing as projected on a direction in said plane.

20. A combination according to claim 19 wherein said direction is that of the major axis of said ellipse.

21. A nuclear magnetic resonance imaging apparatus including a combination of radio frequency transmitting and receiving coil according to claim 1.

* * * * *